(12) United States Patent
Lee et al.

(10) Patent No.: US 8,173,158 B2
(45) Date of Patent: May 8, 2012

(54) METHODS OF TREATING GASTROINTESTINAL DISORDERS INDEPENDENT OF THE INTAKE OF FOOD

(75) Inventors: Ronald D. Lee, Round Lake Beach, IL (US); Majid Vakily, Gurnee, IL (US); Darcy Mulford, Grayslake, IL (US); Jing-Tao Wu, Mundelein, IL (US); Stuart Atkinson, Lake Forest, IL (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 523 days.

(21) Appl. No.: 12/249,258

(22) Filed: Oct. 10, 2008

(65) Prior Publication Data

US 2009/0098199 A1 Apr. 16, 2009

Related U.S. Application Data

(60) Provisional application No. 60/998,754, filed on Oct. 12, 2007.

(51) Int. Cl.
*A61K 9/48* (2006.01)
*A61K 9/60* (2006.01)
(52) U.S. Cl. ......... 424/451; 424/459; 424/463; 424/490
(58) Field of Classification Search ................... None
See application file for complete search history.

(56) References Cited

U.S. PATENT DOCUMENTS

| | | | |
|---|---|---|---|
| 2,957,880 A | 10/1960 | Romesh | |
| 2,996,431 A | 8/1961 | Barry | |
| 4,182,756 A | 1/1980 | Ramsay | |
| 4,464,170 A | 8/1984 | Clemens | |
| 4,600,577 A | 7/1986 | Didriksen | |
| 4,628,098 A | 12/1986 | Nohara et al. | |
| 4,728,512 A | 3/1988 | Mehta | |
| 4,773,907 A | 9/1988 | Urquhart | |
| 4,777,049 A | 10/1988 | Magruder | |
| 4,783,337 A | 11/1988 | Wong et al. | |
| 4,786,505 A | 11/1988 | Lovgren et al. | |
| 4,853,230 A | 8/1989 | Lovgren et al. | |
| 4,863,742 A | 9/1989 | Panoz et al. | |
| 4,871,549 A | 10/1989 | Ueda | |
| 4,894,240 A | 1/1990 | Geoghegan et al. | |
| 4,904,476 A | 2/1990 | Mehta et al. | |
| 4,980,170 A | 12/1990 | Schneider et al. | |
| 5,011,692 A | 4/1991 | Fujioka | |
| 5,017,381 A | 5/1991 | Maruyama | |
| 5,026,560 A | 6/1991 | Makino et al. | |
| 5,045,321 A | 9/1991 | Makino et al. | |
| 5,093,132 A | 3/1992 | Makino et al. | |
| 5,133,974 A | 7/1992 | Paradissis et al. | |
| 5,178,867 A | 1/1993 | Guittard et al. | |
| 5,178,878 A | 1/1993 | Wehling et al. | |
| 5,229,131 A | 7/1993 | Amidon et al. | |
| 5,229,134 A | 7/1993 | Mention et al. | |
| 5,260,068 A | 11/1993 | Chen | |
| 5,260,069 A * | 11/1993 | Chen ............................ | 424/451 |
| 5,264,223 A | 11/1993 | Yamamoto et al. | |
| 5,330,982 A | 7/1994 | Tyers | |
| 5,348,748 A | 9/1994 | Sheth et al. | |
| 5,401,512 A * | 3/1995 | Rhodes et al. ................ | 424/458 |
| 5,431,917 A | 7/1995 | Yamamoto et al. | |
| 5,433,959 A | 7/1995 | Makino et al. | |
| 5,445,829 A | 8/1995 | Paradissis et al. | |
| 5,476,669 A | 12/1995 | Borody | |
| 5,516,351 A | 5/1996 | Solomon et al. | |
| 5,578,732 A | 11/1996 | Kato et al. | |
| 5,582,837 A | 12/1996 | Shell | |
| 5,631,020 A | 5/1997 | Okada et al. | |
| 5,631,021 A | 5/1997 | Okada et al. | |
| 5,639,476 A | 6/1997 | Oshlack et al. | |
| 5,639,478 A | 6/1997 | Makino et al. | |
| 5,643,607 A | 7/1997 | Okada et al. | |
| 5,652,146 A | 7/1997 | Kell | |
| 5,656,290 A | 8/1997 | Kelm et al. | |
| 5,716,640 A | 2/1998 | Kamei et al. | |
| 5,726,316 A | 3/1998 | Crooks et al. | |
| 5,753,265 A | 5/1998 | Bergstrand et al. | |
| 5,763,396 A | 6/1998 | Weiner et al. | |
| 5,807,577 A | 9/1998 | Ouali | |
| 5,814,342 A | 9/1998 | Okada et al. | |
| 5,817,338 A | 10/1998 | Bergstrand et al. | |
| 5,817,388 A | 10/1998 | Hurditch | |
| 5,834,024 A | 11/1998 | Heinicke et al. | |
| 5,837,284 A | 11/1998 | Mehta et al. | |

(Continued)

FOREIGN PATENT DOCUMENTS

DE 4035455 11/1990

(Continued)

OTHER PUBLICATIONS

Singh B.N. Modified-release solid formulations for colonic delivery. Recent Patents on Drug Delivery & Formulations (2007) 1:53-65.*
J. Cronlein, K. Fegely, C. Young, and A. Rajabi-Siahboomi. Characterization of Delayed Release Lansoprazole Multiparticulates: Impact of Biorelevant Dissolution Media. 5th World Meeting on Pharmaceutics 2006 (March). Poster Reprint.*
International Search Report for PCT/US08/79520.
Written Opinion of the International Searching Authority for PCT/US08/79520.
Physician's Desk Reference—Lansoprazole (1997)—5 pages.
Arimori et al., J. Pharma. Pharmacology, 50:1241-1254 (1998).
Atwood et al., Chem. Commun., 2736-2377 (2001).
Chemical Abstracts vol. 127, Nos. 1-2 Abstracts 1-28414 (1997) (2 pages).
Chemical & Engineering News, pp. 31-35 (2003).
Barradell et al., "Lansoprazole: a review of its pharmacodynamic and pharmacokinetic properties and its therapeutic efficacy in acid-related disorders," Drugs (1992) 44(2):225-250.

(Continued)

*Primary Examiner* — Robert A Wax
*Assistant Examiner* — Olga V Tcherkasskaya
(74) *Attorney, Agent, or Firm* — Lisa V. Mueller; Michael Best & Friedrich LLP

(57) ABSTRACT

The present invention relates to a method of treating a gastrointestinal disorder by administering to a patient in need of treatment thereof a pharmaceutical composition, wherein said pharmaceutical composition can be administered to the patient independent of the intake of food.

12 Claims, 2 Drawing Sheets

U.S. PATENT DOCUMENTS

| | | | |
|---|---|---|---|
| 5,879,708 A | 3/1999 | Makino et al. | |
| 5,889,051 A | 3/1999 | Chen et al. | |
| 5,900,252 A * | 5/1999 | Calanchi et al. | 424/459 |
| 5,945,124 A | 8/1999 | Sachs et al. | |
| 5,948,789 A | 9/1999 | Larsson et al. | |
| 6,036,976 A | 3/2000 | Takechi et al. | |
| 6,096,339 A | 8/2000 | Ayer et al. | |
| 6,110,494 A | 8/2000 | Clancy et al. | |
| 6,126,969 A | 10/2000 | Shah et al. | |
| 6,162,463 A | 12/2000 | Lippa | |
| 6,274,173 B1 | 8/2001 | Sachs et al. | |
| 6,328,994 B1 | 12/2001 | Shimizu et al. | |
| 6,369,085 B1 | 4/2002 | Cotton et al. | |
| 6,462,058 B1 | 10/2002 | Fujishima et al. | |
| 6,605,303 B1 | 8/2003 | Karehill et al. | |
| 6,610,323 B1 | 8/2003 | Lundberg et al. | |
| 6,635,276 B1 | 10/2003 | Von Falkenhausen | |
| 6,635,280 B2 | 10/2003 | Shell et al. | |
| 6,664,276 B2 | 12/2003 | Fujishima et al. | |
| 6,897,205 B2 * | 5/2005 | Beckert et al. | 514/159 |
| 6,939,971 B2 | 9/2005 | Fujishima et al. | |
| 6,982,275 B2 | 1/2006 | Hashimoto et al. | |
| 7,147,869 B2 | 12/2006 | Dietrich et al. | |
| 7,169,799 B2 | 1/2007 | Hashimoto et al. | |
| 7,271,182 B2 | 9/2007 | Kamiyama et al. | |
| 7,285,668 B2 | 10/2007 | Hashimoto et al. | |
| 7,339,064 B2 | 3/2008 | Fujishima et al. | |
| 7,569,697 B2 | 8/2009 | Fujishima et al. | |
| 7,737,282 B2 | 6/2010 | Fujishima et al. | |
| 7,790,755 B2 | 9/2010 | Akiyama et al. | |
| 8,030,333 B2 | 10/2011 | Fujishima et al. | |
| 2002/0034541 A1 | 3/2002 | Valducci | |
| 2002/0042433 A1 | 4/2002 | Yelle et al. | |
| 2003/0008903 A1 | 1/2003 | Barberich et al. | |
| 2003/0091630 A1 | 5/2003 | Louie-Helm et al. | |
| 2003/0153766 A1 | 8/2003 | Hashimoto et al. | |
| 2003/0171591 A1 | 9/2003 | Hashimoto et al. | |
| 2003/0181487 A1 | 9/2003 | Kamiyama et al. | |
| 2004/0049045 A1 | 3/2004 | Hashimoto et al. | |
| 2004/0146558 A1 | 7/2004 | Hirata et al. | |
| 2005/0003005 A1 | 1/2005 | Shimizu et al. | |
| 2005/0226929 A1 | 10/2005 | Xie et al. | |
| 2005/0228026 A1 | 10/2005 | Fujishima et al. | |
| 2006/0018964 A1 | 1/2006 | Combessis et al. | |
| 2006/0024362 A1 | 2/2006 | Seth | |
| 2006/0057195 A1 * | 3/2006 | Nonomura et al. | 424/464 |
| 2008/0193522 A1 | 8/2008 | Meier et al. | |
| 2008/0193540 A1 | 8/2008 | Soula et al. | |
| 2008/0200482 A1 | 8/2008 | Petereif et al. | |
| 2009/0098199 A1 * | 4/2009 | Lee et al. | 424/451 |
| 2009/0215830 A1 | 8/2009 | Taneja | |
| 2009/0220611 A1 | 9/2009 | Dargelas et al. | |
| 2009/0263475 A1 * | 10/2009 | Manne et al. | 424/451 |
| 2010/0068291 A1 | 3/2010 | Caisse et al. | |
| 2010/0272798 A1 | 10/2010 | Akiyama et al. | |
| 2010/0278911 A1 | 11/2010 | Akiyama et al. | |
| 2010/0285120 A1 | 11/2010 | Akiyama et al. | |
| 2011/0189271 A1 * | 8/2011 | Lad et al. | 424/451 |
| 2011/0223244 A1 * | 9/2011 | Liversidge et al. | 424/452 |
| 2011/0274752 A1 * | 11/2011 | Cifter et al. | 424/465 |
| 2011/0274753 A1 * | 11/2011 | Cifter et al. | 424/465 |
| 2011/0274754 A1 * | 11/2011 | Cifter et al. | 424/468 |

FOREIGN PATENT DOCUMENTS

| | | |
|---|---|---|
| EP | 0274734 | 7/1988 |
| EP | 0694547 | 1/1996 |
| EP | 0924519 | 6/1999 |
| EP | 0960620 | 12/1999 |
| EP | 1044682 | 10/2000 |
| EP | 1607088 | 12/2005 |
| JP | 59227817 | 12/1984 |
| JP | 60-228410 | 11/1985 |
| JP | 2552937 | 12/1991 |
| JP | 2000355540 | 12/2000 |
| JP | 2001122769 | 5/2001 |
| WO | WO 93/18755 | 9/1993 |
| WO | WO 96/01623 | 1/1996 |
| WO | WO 96/02535 | 2/1996 |
| WO | WO 96/17077 | 6/1996 |
| WO | WO 96/24338 | 8/1996 |
| WO | WO 97/02020 | 1/1997 |
| WO | WO 97/02261 | 1/1997 |
| WO | WO 97/25064 | 7/1997 |
| WO | WO 97/32573 | 9/1997 |
| WO | WO 97/48380 | 12/1997 |
| WO | WO 98/21201 | 5/1998 |
| WO | WO 98/22118 | 5/1998 |
| WO | WO 98/28294 | 7/1998 |
| WO | WO 99/03453 | 1/1999 |
| WO | WO 99/32091 | 7/1999 |
| WO | WO 99/32093 | 7/1999 |
| WO | WO 99/38512 | 8/1999 |
| WO | WO 99/38513 | 8/1999 |
| WO | WO 99/51203 | 10/1999 |
| WO | WO 99/56698 | 11/1999 |
| WO | WO 99/58107 | 11/1999 |
| WO | WO 00/09092 | 2/2000 |
| WO | WO 00/25752 | 5/2000 |
| WO | WO 01/37808 | 5/2001 |
| WO | WO 02/39980 | 5/2002 |
| WO | WO 02/060415 | 8/2002 |
| WO | WO 03/086366 | 10/2003 |
| WO | WO 2004/035020 | 4/2004 |
| WO | WO 2004/035052 | 4/2004 |
| WO | WO 2004/045580 | 6/2004 |
| WO | WO 2004/093875 | 11/2004 |
| WO | WO 2006/009602 | 1/2006 |
| WO | WO 2006/044202 | 4/2006 |
| WO | WO 2006/056712 | 6/2006 |
| WO | WO 2006/122925 | 11/2006 |
| WO | WO 2006/125483 | 11/2006 |
| WO | WO 2007/006353 | 1/2007 |
| WO | WO 2007/036671 | 4/2007 |

OTHER PUBLICATIONS

Katsuki et al., "Determination of R(+)- and S(−)-Lansoprazole using chiral stationary-phase liquid chromatography and their enantioselective pharmacokinetics in humans," Pharm. Res. (1996) 13(4):611-615.

Nagaya et al., "Effects of the enantiomers of lansoprazole (AG-1749) on H++K+)-ATPase activity in canine gastric microsomes and acid formation in isolated canine parietal cells," Biochem. Pharm. (1991) 42(10):1875-1878.

Sharma, V.K. et al., "Oral pharmacokinetics of omeprazole and lansoprazole after single and repeated doses as intact capsules or as suspensions in sodium bicarbonate," Aliment Pharmacol. Ther. (2000) 14:887-892.

International Search Report and Written Opinion for Application No. PCT/US2005/019028 dated Jun. 13, 2006 (10 pages).

U.S. Appl. No. 11/629,016 dated Nov. 23, 2010 (11 pages).

U.S. Appl. No. 11/629,016 dated Mar. 17, 2010 (9 pages).

Balvanera, A. et al., "A normal coronary arteriogram in a very young man with Prinzmetal's variant angina: case report with review of the literature," Cardiovasc. Dis.,Bulletin of the Texas Heart Institute (1981) 8(4):537-545.

Borner, K. et al., "Separation of lansoprazole enantiomers in human serum by HPLC," Chromat. (1998) 47(3-4):171-175.

Bowler, I.M. et al., "A double blind lipase for lipase comparison of a high lipase and standard pancreatic enzyme preparation in cystic fibrosis," Arch. Dis. In Childhood (1993) 68:227-230.

Brittain, H.G., "Methods for the characterization of polymorphs and solvates," in Polymorphism in Pharmaceutical Solids, Marcel Dekker, Inc., New York (1999) Chapter 6, 227-278.

Concise Encyclopedia, "Polymorphism" H.D. Jakubke et al. editors (1993) 872-873.

Efron et al., "Side effects of methylphenidate and dexamphetamine in children with attention deficit hyperactivity disorder: a double-blind,crossover trial," Pediatrics 100:662-666 (1997).

Figulla, H.R. et al., "Diltiazem improves cardiac function and exercise capacity in patients with idiopathic dilated cardiomyopathy: results of the diltiazem in dilated cardiomyopathy trial," Circulation (1996) 94(3):346-352.

Gerkensmeier, T. et al., "Self-assembly of 2,8,14,20-tetraisobutyl-5,11,17,23-tetrahydroxyresorc[4]arene," Eur. J. Org. Chem. (1999) 2257-2262.

Gordon, A.J. et al., The Chemist's Companion, A Handbook of Practical Data, Techniques, and References, John Wiley & Sons, New York (1972) 440-445.

Gottdiener, J.S. et al., "Effect of single-drug therapy on reduction of left atrial size in mild to moderate hypertension: comparison of six antihypertensive agents," Circulation (1998) 98:140-148.

Haleblian, J. et al., "Pharmaceutical Applications of Polymorphism," J. Pharm. Sci. (1969) 58(8):911-929.

Handbook of Pharmaceutical Excipients, 4th Edition, R.C. Rowe et al., editors, Pharmaceutical Press, London (2003) 120-124; 301-305; 462-468; 538-540.

Hirschowitz, B.I. et al., "Long-term treatment with lansoprazole for patients with Zollinger-Ellison syndrome," Aliment Pharmacol. Ther. (1996) 10:507-522.

Katsuki, H. et al., "Determination of R(+)- and S(31 )-lansoprazole using chiral stationary-phase liquid chromatography and their enantioselective pharmacokinetics in humans," Pharm. Res. (1996) 13:611-615.

Kotar, B. et al., "Study of polymorphism of a novel antiulcer drug," Poster Session P3: Tuesday Sep. 17, S182.

Lin, A.Y. et al., "Study of crystallization of endogenous surfactant in eudragit NE30D-free films and its influence on drug-release properties of controlled-release diphenhydramine HCI pellets coated with eudragit NE30D," AAPS Pharmsci. (2001) 3:1-12.

Marvola, M. et al., "Enteric polymers as binders and coating materials in multiple-unit site-specific drug delivery systems," Eur. J. Pharm. Sci. (1999) 7:259-267.

Mikawa, K. et al., "Lansoprazole reduces preoperative gastric fluid acidity and volume In children," Can. J. Anaesth. (1995) 42(6):467-472.

Ogura, T. et al., "HPMC capsules—an alternative to gelatin," Pharmaceutical Technology Europe (1998) 10(11):32-42.

Physician's Desk Reference, "Prevacid," 55th Edition, Medical Economics Company, Inc., New Jersey (2001) 6 pages.

Remington: The Science and Practice of Pharmacy, 20th Ed., A.R. Gennaro, Editor (2000) p. 897 and 903.

Robinson, M. et al., "Effective maintenance treatment of reflux esophagitis with low-dose lansoprazole. A randomized, double-blind, placebo-controlled trial," Annals of Int. Med. (1996) 124(10):859-867.

Rouhi, A.M., "Concentrates" and "The right stuff. From research and development to the clinic, getting drug crystals right is full of pitfalls," Chemical and Engineering News (2003) 31-35.

Sakamoto, T. et al., "Prolonged action preparation of cefaclor," Jap. J. Antibiotics (1985) 38(3):813-821 (Abstract and figures in English).

Srinivas, N.R. et al., "Enantioselective pharmacokinetics of dl-threo-methylphenidate in humans," Pharm. Res. (1993) 10(1):14-21.

Tietze et al. "Isolation and purification of reaction products," Chapter 1.5 of Reactions and Syntheses in the Organic Chemistry Laboratory (1989) 23-26.

United States Pharmacopeia, The, "Lansoprazole" The National Formulary USP 32, NF 27 (2009) 2:2751-2754.

United States Pharmacopeia, The, "X-ray diffraction," The National Formulary USP 25 NF 20 (2002) 2088-2089.

United States Pharmacopeia, The, "X-ray diffraction," The National Formulary USP23 NF 18 (1995) 1843-1844.

United States Pharmacopeia, The, "X-ray diffraction," The National Formulary USP28 NF 23 (2005) 2513-2514.

Vrecer, F. et al., "Study of influence of temperature and grinding on the crystalline state of lansoprazole," Farm. Vestn. (1997) 242-243—Chemical Abstracts No. 127:362535, 63-Pharmaceuticals (1997) 127(26):751.

Wilkins, C.E. et al., "HIV-associated myocarditis treated with zidovudine (AZT)," Tex Heart Inst. J. (1989) 16:44-45.

Yukawa, E., "Optimisation of antiepileptic drug therapy," *Clin. Pharmacokinet.* (1996) 31(2):120-130.

Abel, C., et al., "Dexlansoprazole in the treatment of esophagitis and gastroesophageal reflux disease," The Annals of Pharmacotherapy, vol. 44, May, 2010; pp. 871-877.

Lee, R.D., et al., "Clinical trial: the effect and timing of food on the pharmacokinetics and pharmacodynamics of dexlansoprazole MR, a novel dual delayed released formulation of a proton pump inhibitor—evidence for dosing flexibility," Alimentary Pharmacology & Therapeutics, vol. 29, 2009, pp. 824-833.

Metz, D.C., et al., "Review article: dual delayed release formulation of dexlansoprazole MR, a novel approach to overcome the limitations of conventional single release proton pump inhibitor therapy," Alimentary Pharmacology & Therapeutics, vol. 29, 2009, pp. 928-937.

* cited by examiner

METHODS OF TREATING GASTROINTESTINAL DISORDERS INDEPENDENT OF THE INTAKE OF FOOD

RELATED APPLICATION INFORMATION

This application claims priority to U.S. Application No. 60/998,754 filed on Oct. 12, 2007, the contents of which are herein incorporated by reference.

FIELD OF THE INVENTION

The present invention relates to a method of treating a gastrointestinal disorder by administering to a patient in need of treatment thereof a pharmaceutical composition, wherein said pharmaceutical composition can be administered to the patient independent of the intake of food. Specifically, the pharmaceutical composition used in said method comprises at least two solid particles each of which contain at least one proton pump inhibitor.

BACKGROUND OF THE INVENTION

The stomach is an organ of digestion. It has a saclike shape and is located between the esophagus and the intestines. Almost every animal has a stomach.

The human stomach is a muscular, elastic, pear-shaped bag, lying crosswise in the abdominal cavity beneath the diaphragm. It changes size and shape according to its position within the body and the amount of food inside. The wall of the stomach is lined with millions of gastric glands, which together secrete 400-800 ml of gastric juice at each meal. Three kinds of cells are found in the gastric glands. These cells are parietal cells, "chief" cells and mucus-secreting cells. Parietal cells contain an enzyme known as $H^+/K^+$ adenosine triphosphatase. $H^+/K^+$ adenosine triphosphatase is also referred to as an "acid pump" or "proton pump". This transmembrane protein secretes $H^+$ ions (protons) by active transport, using the energy of ATP. The concentration of $H^+$ in the gastric juice can be as high as 0.15 M, giving gastric juice a pH less than 1.

Proton pump inhibitors (or "PPIs") are a class of pharmaceutical compounds that inhibit gastric acid secretions by inhibiting $H^+/K^+$ adenosine triphosphatase. It is known in the art that proton pumps can exist in either an active state or a dormant state. PPIs only bind to the active proton pumps. PPIs are metabolized in the parietal cells to active sulfenamide metabolites that inactivate the sulfhydryl group of the proton pump, thereby reducing the hydrogen ion secretion (Langtry and Wilde, "An update of its pharmacological properties and clinical efficacy in the management of acid-related disorders," *Drugs*, 54(3): 473-500 (1997)).

PPIs are frequently prescribed for short-term treatment of active duodenal ulcers, gastric ulcers, gastroesophageal reflux disease (GERD), severe erosive esophagitis, poorly responsive systematic GERD, and pathological hypersecretory conditions such as Zollinger Ellison syndrome. These conditions are caused by an imbalance between acid and pepsin production (aggressive factors), and mucous, bicarbonate and prostaglandin production (defensive factors). The above listed conditions can arise in healthy or critically ill patients, and may be accompanied by significant gastrointestinal bleeding.

Lansoprazole, a PPI, sold commercially under the brand name PREVACID®, is a substituted benzimidazole, 2-[[[3-methyl-4-(2,2,2-trifluoroethoxy)-2-pyridyl]methyl]sulfinyl] benzimidazole. Lansoprazole is a racemic compound, containing a R-enantiomer and a S-enantiomer. The R-enantiomer of lansoprazole, also known as dexlansoprazole, is also a PPI (See, WO 2004/035020).

PPIs are dosed to patients in need of treatment thereof in conjunction with the intake or consumption of food or a meal. For example, the labeling for PREVACID® (lansoprazole) states that PREVACID® "should be taken before eating" and the labeling for NEXIUM® (esomeprazole magnesium), also a PPI, states that "NEXIUM® should be taken at least one hour before meals." Therefore, patients are unable to take PPIs whenever it is convenient for them to do so, but instead must remember to take their medication with the intake or consumption of food or at least one hour before the intake or consumption of food. In order to improve patience compliance, there is a need in the art for pharmaceutical compositions containing PPIs, such as dexlansoprazole, that can be dosed to a patient independently of the intake or consumption of food.

SUMMARY OF THE INVENTION

In one embodiment, the present invention relates to a method of treating a gastrointestinal disorder in a patient in need of treatment thereof. The method comprises the steps of:
  administering to said patient a pharmaceutical composition comprising a therapeutically effective amount a proton pump inhibitor, wherein said pharmaceutical composition is capable of being administered to a patient independent of the intake of food.

In another embodiment, the present invention relates to a method of treating a gastrointestinal disorder in a patient in need of treatment thereof. The method comprises the steps of:
  administering to said patient a pharmaceutical composition comprising a therapeutically effective amount of:
  (a) a first solid particle, wherein said first solid particle comprises an active agent and a first enteric coating, wherein the first enteric coating releases the active agent from the solid particle at a pH of about 5.0 to about 5.5; and
  (b) a second solid particle, wherein said second solid particle comprises an active agent and a second enteric coating, wherein the second enteric coating releases the active agent from the solid particle at a pH of about 6.2 to about 6.8;
  wherein the first solid particle comprises from about 15% to about 50% by weight of the pharmaceutical composition and the second solid particle comprises from about 50% to about 85% by weight of the pharmaceutical composition; and
  further wherein said pharmaceutical composition is capable of being administered to a patient independent of the intake of food.

In the above method, the first solid particle can be a granule. Additionally, the second solid particle can be a granule. Preferably, both the first and second solid particles are each granules. Preferably, the pharmaceutical composition is a tablet or capsule.

The active agent in the first solid particle can be dexlansoprazole. The active agent in the second solid particle can be dexlansoprazole. Preferably, the active agent in the first solid particle and the second solid particle is dexlansoprazole.

Preferably, the first enteric coating has a pH of about 5.5 and comprises a methacrylic acid copolymer dispersion. Preferably, the second enteric coating has a pH of about 6.75 and comprises a mixture of a methacrylic copolymer Type B and a methacrylic copolymer Type A in a ratio of 3:1.

Optionally, the first solid particle comprises a protective layer between the active agent and the first enteric coating. Optionally, the second solid particle comprises a protective layer between the active agent and the second enteric coating. If present, the protective layer can be made from a saccharide, a saccharide starch or any combinations thereof.

In the above method, the first solid particle comprises about 25% of the pharmaceutical composition and the second solid particle comprises about 75% of the pharmaceutical composition.

The gastrointestinal conditions that can be treated pursuant to the above method include, but are not limited to, heartburn, inflammatory bowel disease, Crohn's disease, irritable bowel syndrome, ulcerative colitis, a peptic ulcer, a stress ulcer, a bleeding peptic ulcer, a duodenal ulcer, infectious enteritis, colitis, diverticulitis, gastric hyperacidity, dyspepsia, gastroparesis, Zollinger-Ellison syndrome, gastroesophageal reflux disease, *Helicobacter pylori* associated disease, short-bowel syndrome, hypersecretory states associated with systemic mastocytosis or basophilic leukemia or hyperhistaminemia or combinations of any of the above disorders.

In a second embodiment, the present invention relates to a method of treating a gastrointestinal disorder in a patient in need of treatment thereof. The method comprising the steps of:
administering to said patient a capsule comprising a therapeutically effective amount of:
(a) a first granule, wherein said first granule comprises dexlansoprazole and a first enteric coating, wherein the first enteric coating releases the dexlansoprazole from the granule at a pH of about 5.5; and
(b) a second granule, wherein said second granule comprises dexlansoprazole and a second enteric coating, wherein the second enteric coating releases the dexlansoprazole from the solid particle at a pH of about 6.75;
wherein the first granule comprises about 25% of the capsule and the second granule comprises from about 75% of the capsule; and
further wherein said capsule is capable of being administered to a patient independent of the intake of food.

In the above method, first enteric coating comprises a methacrylic acid copolymer dispersion and the second enteric coating comprises a mixture of a methacrylic copolymer Type B and a methacrylic copolymer Type A in a ratio of 3:1. Additionally, in the above method, the first granule can further comprise a protective layer between the dexlansoprazole and the first enteric coating and the second granule can further comprise a protective layer between the dexlansoprazole and the second enteric coating. The protective layer contained in each of these granules can be made of a saccharide, a saccharide starch or any combinations thereof.

The gastrointestinal conditions that can be treated pursuant to the above method include, but are not limited to, heartburn, inflammatory bowel disease, Crohn's disease, irritable bowel syndrome, ulcerative colitis, a peptic ulcer, a stress ulcer, a bleeding peptic ulcer, a duodenal ulcer, infectious enteritis, colitis, diverticulitis, gastric hyperacidity, dyspepsia, gastroparesis, Zollinger-Ellison syndrome, gastroesophageal reflux disease, *Helicobacter pylori* associated disease, short-bowel syndrome, hypersecretory states associated with systemic mastocytosis or basophilic leukemia or hyperhistaminemia or combinations of any of the above disorders.

DETAILED DESCRIPTION OF THE INVENTION

Definitions

Figure 1:
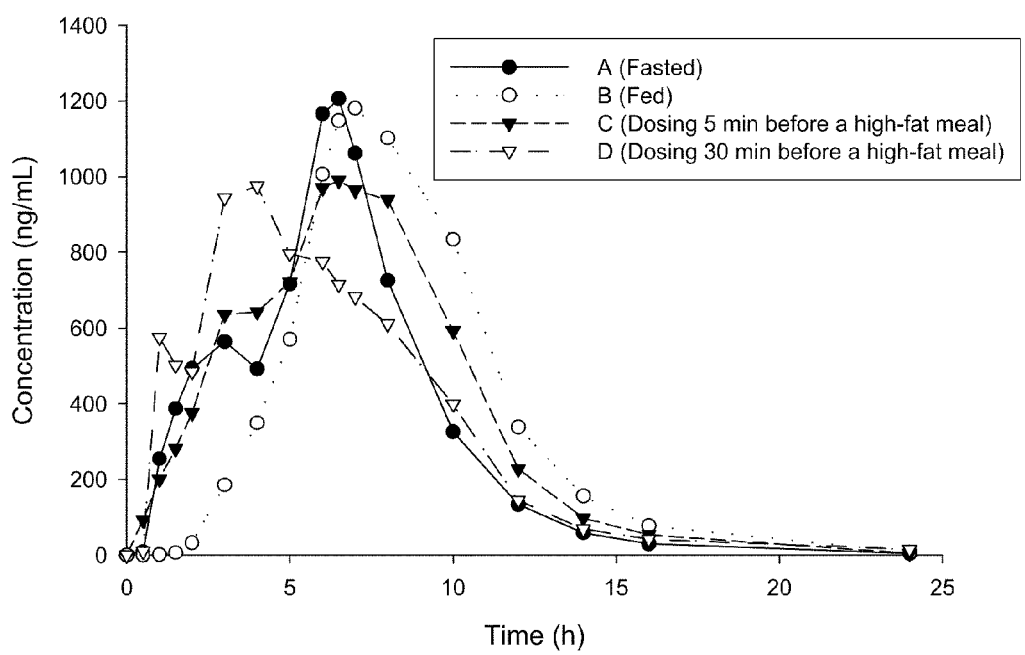
FIG. 1 shows the mean plasma TAK-390 MR concentration vs time profiles for each of Regimens A-D as described in Example 2.

As used in this specification and the appended claims, the singular forms "a," "an" and "the" include plural references unless the context clearly dictates otherwise. Thus, for example, reference to "an active agent" includes a single active agent as well two or more different active agents in combination.

In describing and claiming the present invention, the following terminology will be used in accordance with the definitions set out below.

The terms "active agent," "active ingredient," and "drug" are used interchangeably herein to refer to compounds of the general formula I (below), an alkaline salt thereof, a metabolite thereof or a prodrug thereof, one of the single enantiomers thereof, an alkaline salt thereof (such as, for example, $Mg^{2+}$, $Ca^{2+}$, $Na^+$ or $K^+$ salts), a metabolite thereof or a prodrug thereof or a single enantiomer of the compounds of the general formula I, an alkaline salt of a single enantiomer of compounds of the general formula I, a metabolite of a single enantiomer of compounds of general formula I or a prodrug of a single enantiomer of compounds of general formula I:

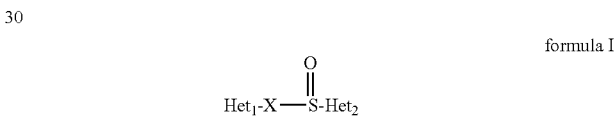

formula I wherein $Het_1$ is

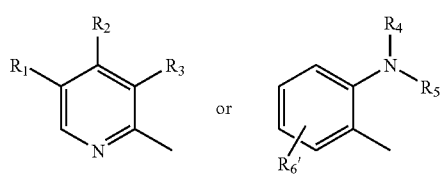

$Het_2$ is

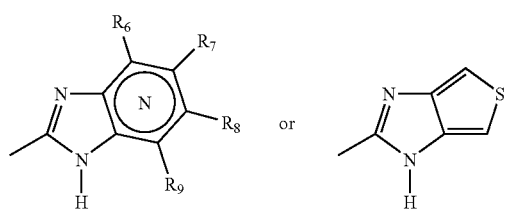

X is

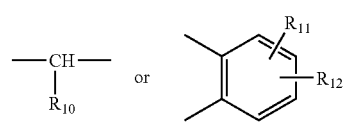

wherein
- N in the benzimidazole moiety means that one of the ring carbon atoms substituted by $R_6$-$R_9$ optionally may be exchanged for a nitrogen atom without any substituents;
- $R_1$, $R_2$ and $R_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;
- $R_4$ and $R_5$ are the same or different and selected from hydrogen, alkyl and arylalkyl;
- $R_6'$ is hydrogen, halogen, trifluoromethyl, alkyl or alkoxy;
- $R_6$-$R_9$ are the same or different and selected from hydrogen, alkyl, alkoxy, halogen, haloalkoxy, alkylcarbonyl, alkoxycarbonyl, oxazolinyl, trifluoroalkyl, a heterocyclic ring that may be further substituted or adjacent groups $R_6$-$R_9$ form ring structures which may be further substituted;
- $R_{10}$ is hydrogen; and
- $R_{11}$ and $R_{12}$ are the same or different and selected from hydrogen, halogen or alkyl.

Preferred compounds according to formula I are:

(Omeprazole)

(Esomeprazole magnesium)

(Lansoprazole)

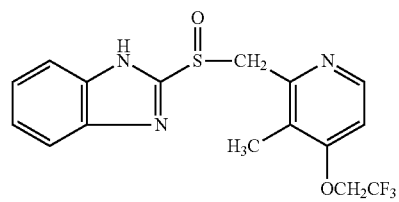

(Dexlansoprazole)

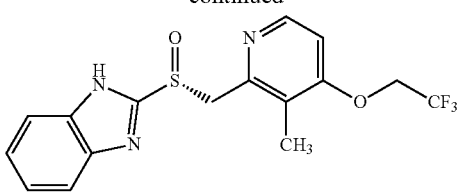

(Pantoprazole)

(Rabeprazole)

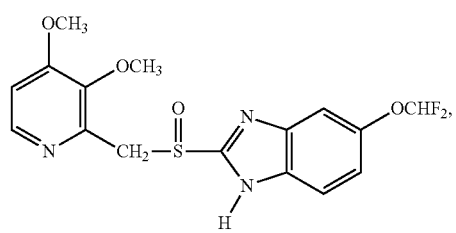

(Tenatoprazole)

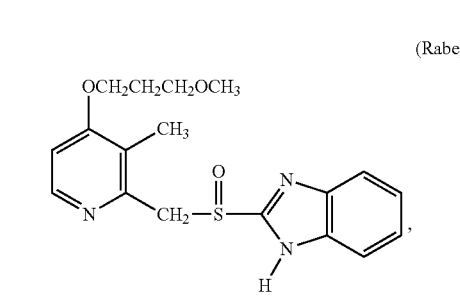

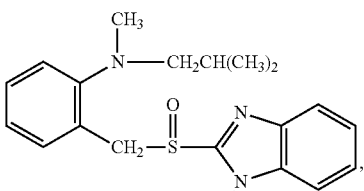

and (Ilaprazole)

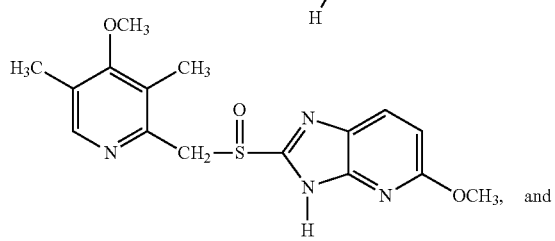

The most preferred compound of formula I is dexlansoprazole, the R-enantiomer of lansoprazole.

The terms "administer", "administering", "administered" or "administration" refer to any manner of providing a drug to a subject or patient. Routes of administration can be accomplished through any means known by those skilled in the art. Such means include, but are not limited to, oral, buccal, intravenous, subcutaneous, intramuscular, by inhalation and the like.

As used herein, the term "bioavailability" refers to the rate, extent, and duration with which an active ingredient or drug enters and remains in the general circulation, thereby permitting access to the site of action. Higher bioavailability may be achieved, for example, by increasing the active ingredient or drug's duration of action. Methods to determine the bioavailability of active ingredients or drugs are well known to those of ordinary skill in the art.

As used herein, the term "chronic cough" refers to a cough that last for a period of at least one (1) week, preferably at least two (2) weeks and most preferably at least three (3) weeks. Methods of treating chronic cough using PPIs are disclosed in Chung, *Clinc. Exp. Allergy*, 35:245-246 (2005).

The term "dosage form" refers to any solid object, semi-solid, or liquid pharmaceutical composition designed to contain a specific pre-determined amount (i.e. dose) of a certain active ingredient. Suitable dosage forms may be pharmaceutical drug delivery systems, including those for oral administration, buccal administration, rectal administration, topical or mucosal delivery or subcutaneous implants, or other implanted drug delivery systems and the like. Preferably, the dosage form of the pharmaceutical composition of the present invention is considered to be solid; however, they may contain liquid or semi-solid components.

By an "effective amount" or a "therapeutically effective amount" of a dosage form is meant a nontoxic but sufficient amount of the active ingredient to provide the desired effect. The amount of active ingredient that is "effective" will vary from subject to subject, depending on the age and general condition of the individual, the particular active ingredient or active ingredient, and the like. Thus, it is not always possible to specify an exact "effective amount." However, an appropriate "effective amount" in any individual case may be determined by one of ordinary skill in the art using routine experimentation.

As used herein, the term "gastrointestinal disorder" refers to any disease or disorder of the upper and lower gastrointestinal tract of a patient including, for example, heartburn, inflammatory bowel disease, Crohn's disease, irritable bowel syndrome, ulcerative colitis, peptic ulcers, stress ulcers, bleeding peptic ulcers, duodenal ulcers, infectious enteritis, colitis, diverticulitis, gastric hyperacidity, dyspepsia, gastroparesis, Zollinger-Ellison syndrome, gastroesophageal reflux disease ("GERD") (i.e., acid reflux), including, but not limited to, symptomatic GERD and asymptomatic GERD, *Helicobacter pylori* associated-diseases, hypersecretory states associated with systemic mastocytosis or basophilic leukemia and hyperhistaminemia that result, for example, from neurosurgery, head injury, severe body trauma or burns.

As used herein, the term "lower gastrointestinal tract" refers to the ileum, the colon, the cecum and the rectum.

The term "patient" refers to an animal, preferably a mammal, including a human or non-human. The terms patient and subject may be used interchangeably herein.

By "pharmaceutically acceptable," such as in the recitation of a "pharmaceutically acceptable excipient," or a "pharmaceutically acceptable additive," is meant a material that is not biologically active or otherwise undesirable, i.e., the material may be incorporated into a pharmaceutical composition administered to a patient without causing any undesirable biological effects.

As used herein, the term "stabilizer" refers to any chemical, compound or material that minimizes the degradation of the active ingredient or drug by the acidic environment of the stomach. Examples of stabilizers include, but are not limited to, aluminum salts, carbonate or bicarbonate salts of aluminum, Group IA metals or Group IIA metal salts (such as, but not limited to, sodium salts, calcium salts, magnesium salts, etc.), carbonate or bicarbonate salts of Group IA or Group IIA salts (such as a carbonate or bicarbonate salt of sodium, a carbonate or bicarbonate salt of magnesium, a bicarbonate salt of calcium), polymers, sodium alginate, sterols, fatty alcohols and combinations thereof.

Examples of polymers that can be used as stabilizers include, but are not limited to, semipermeable homopolymers, semipermeable copolymers, and the like. Preferably, the polymers cellulose esters, cellulose ethers and cellulose ester-ethers. The cellulosic polymers have a degree of substitution ("DS") of their anhydroglucose unit from greater than 0 up to 3, inclusive. Degree of substitution means the average number of hydroxyl groups originally present on the anhydroglucose unit that are replaced by a substituting group or converted into another group. The anhydroglucose unit can be partially or completely substituted with groups such as acyl, alkanoyl, alkenoyl, aroyl, alkyl, alkoxy, halogen, carboalkyl, alkylcarbamate, alkylcarbonate, alkylsulfonate, alkysulfamate, semipermeable polymer forming groups, and the like.

Examples of semipermeable polymers include a member selected from the group consisting of cellulose acylate, cellulose diacylate, cellulose triacylate, cellulose acetate, cellulose diacetate, cellulose triacetate, mono-, di- and tri-cellulose alkanylates, mono-, di-, and tri-alkenylates, mono-, di-, and tri-aroylates, and the like. Exemplary polymers include cellulose acetate having a DS of 1.8 to 2.3 and an acetyl content of 32 to 39.9%, cellulose diacetate having a DS of 1 to 2 and an acetyl content of 21 to 35%; cellulose triacetate having a DS of 2 to 3 and an acetyl content of 34 to 44.8%, and the like. More specific cellulosic polymers include cellulose propionate having a DS of 1.8 and a propionyl content of 38.5%, cellulose acetate propionate having an acetyl content of 1.5 to 7% and a propionyl content of 39 to 42%, cellulose acetate propionate having an acetyl content of 2.5 to 3%, an average propionyl content of 39.2 to 45%, and a hydroxyl content of 2.8 to 5.4%, cellulose acetate butyrate having a DS of 1.8, an acetyl content of 13 to 15%, and a butyryl content of 34 to 39%, cellulose acetate butyrate having an acetyl content of 2 to 29%, a butyryl content of 17 to 53%, and a hydroxyl content of 0.5 to 4.7%, cellulose triacylates having a DS of 2.6 to 3, such as cellulose trivalerate, cellulose trilamate, cellulose tripalmitate, cellulose trioctanote and cellulose tripropionate, cellulose diesters having a DS of 2.2 to 2.6, such as cellulose disuccinate, cellulose dipalmitate, cellulose dioctanoate, cellulose dicarpylate, and the like; and mixed cellulose esters, such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be synthesized by procedures described in *Encyclopedia of Polymer Science and Technology*, Vol. 3, pp. 325-354 (1964), Interscience Publishers Inc., New York, N.Y.

Semi-permeable polymers comprise cellulose acetaldehyde dimethyl acetate, cellulose acetate ethylcarbamate, cellulose acetate methyl carbamate, cellulose dimethylaminoacetate, semipermeable polyamide, semipermeable polyurethanes; semipermeable sulfonated polystyrenes, cross-linked selectively semipermeable polymers formed by the coprecipitation of an anion and a cation, as disclosed in U.S. Pat. Nos. 3,173,876, 3,276,586, 3,541,005, 3,541,006 and 3,546,142, semipermeable polymers, as disclosed by Loeb, et al. in U.S. Pat. No. 3,133,132, semipermeable polystyrene derivatives, semipermeable poly(sodium styrenesulfonate), semipermeable poly(vinylbenzyltrimethylammonium chloride); and semipermeable polymers exhibiting a fluid permeability of $10^{-5}$ to $10^{-2}$ (cc. mil/cm hr·atm), expressed as per atmosphere of hydrostatic or osmotic pressure differences across a semipermeable wall. The polymers known to those skilled in the art are described in U.S. Pat. Nos. 3,845,770, 3,916,899 and 4,160,020; and in *Handbook of Common Polymers*, Scott and Roff (1971) CRC Press, Cleveland, Ohio.

Examples of sterols that can be used as stabilizers include, but are not limited to, phytosterols (such as ergosterols, stigmasterol, sitosterol, brassicasterol and campesterol), zoosterols (such as cholesterol and lanosterol) or combinations thereof.

The fatty alcohols that can be used as stabilizers can be linear, saturated or unsaturated primary alcohols having 10-30 carbon atoms. Examples of fatty alcohols that can be used include, but are not limited to, cetyl alcohol, myristyl alcohol or stearyl alcohol.

The terms "treating" and "treatment" refer to a reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

As used herein, the term "ulcers" refers to lesions of the upper gastrointestinal tract lining that are characterized by a loss of tissue. Such ulcers include, but are not limited to, gastric ulcers, duodenal ulcers and gastritis.

As used herein, the term "upper gastrointestinal tract" refers to the esophagus, the stomach, the duodenum and the jejunum.

The fasting pH of the stomach varies between a pH of 2 to 6 (a pH of less than 7 is considered to be an acidic pH). The pH of the small intestine is more alkaline than the pH of the stomach and increases from the duodenum to the ileum. The active ingredient of the present invention, like other PPI's known in the art, is acid labile. It rapidly degrades at an acidic pH to an inactive compound. When a tablet or capsule dissolves in the stomach, this tablet or capsule is thoroughly mixed with the gastric contents of the stomach. Upon transferring from the stomach to the duodenum, the gastric contents are slowly neutralized by bicarbonate present in duodenum. Thus, the pH increases as the gastric contents transition through the small intestine.

The exact location of drug absorption, whether in the stomach, small intestine or throughout the gastrointestinal tract, is uncertain. The inventors of the present invention discovered that the active ingredient exhibits site-specific absorption in the upper part of the small intestine (See Example 4). Specifically, the absorption of the active ingredient is significantly higher in the upper part of the small intestine, namely in the area of the duodenum, in the area of the upper jujunum or a combination of the areas of the duodenum and upper jujunum, where the pH is more acidic.

DESCRIPTION OF THE PRESENT INVENTION

It is known in the art that proton pump inhibitors (PPIs), such as lansoprazole, omeprazole, etc., are orally administered to patients in connection with the intake of food (such as, for example, at the time of ingesting a meal, such as a breakfast). In fact, the labeling for PREVACID® (lansoprazole) states that PREVACID® "should be taken before eating". By way of another example, the labeling for NEXIUM® (esomeprazole magnesium) states that "NEXIUM® should be taken at least one hour before meals." However, the administration of such PPIs in conjunction with the intake of food decreases the systemic exposure of the PPI. The inventors have discovered a method of treating a patient with a pharmaceutical composition containing at least one PPI, wherein the pharmaceutical composition can be administered to the patient independently of food or meal intake or consumption. The inventors have also discovered that administering the pharmaceutical compositions of the present invention to a patient in need of treatment thereof exhibits unexpected and surprising benefits. Specifically, it is known in the art that the administration of PPI's such as PREVACID® with a high fat meal results in an approximately 50% to 70% decrease in the $C_{max}$ and $AUC_\infty$ values, respectively. This is a substantial decrease in the systemic exposure of the PPI after administration with such a high fat meal. Similarly, the administration of NEXIUM° within 15 minutes of a high-fat meal has been shown to have a negative effect on its absorption and bioavailability (both $C_{max}$ and AUC) (See, Sostek M B, et al. *Br J Clin Pharmacol*. 64:386-390 (2007)). However, the inventors have found that the administration of the pharmaceutical compositions of the present invention with a high fat meal leads to an increase in the systemic exposure of the PPI after administration of such a high fat meal. For example, as will be shown herein, the inventors have found that the oral administration of a 90 mg dose of dexlansoprazole with a high fat meal resulted in an approximately 37% increase in the $C_{max}$ and $AUC_\infty$ values, respectively.

The methods of the present invention involve administering to a patient in need of treatment thereof a pharmaceutical composition independent of the intake or consumption of food or a meal. The pharmaceutical composition used in the methods of the present invention contains a therapeutically effective amount of at least two different types of solid particles of at least one active agent. Preferably, the solid particles are one or more granules. While the pharmaceutical composition can contain any number of different types of solid particles, it is preferred that the pharmaceutical composition contain at least two different types of solid particles. The particles comprising the pharmaceutical composition can comprise a single active ingredient or can comprise a mixture of one or more active ingredients. Additionally, each of the different particles can contain a different active ingredient. However, it is preferred that at least one particle contains dexlansoprazole as the active ingredient. It is more preferred that each of the particles contained in the pharmaceutical composition contain the same active ingredient, namely, dexlansoprazole. As mentioned above, the pharmaceutical composition contains at least two solid particles.

In one aspect, the first solid particles comprise an active agent and an enteric coating. In another aspect, the second solid particles comprise an active agent and an enteric coating. In yet another aspect, the first solid particles comprise an active agent and a first enteric coating and the second solid particles comprise an active agent (which can be the same or different than the active agent in the first solid particle, but is preferably the same active agent) and a second enteric coating.

The first solid particle contains a core comprising the active agent and optionally, one or more pharmaceutically acceptable stabilizers (such as, but not limited to, magnesium carbonate), one or more pharmaceutically acceptable polymers, one or more pharmaceutically acceptable binders (such as hydroxylpropylcellulose) one or more pharmaceutically acceptable disintegrants (such as, but not limited to, sodium carboxymethyl cellulose, calcium carboxymethyl cellulose, sodium cross carboxymethyl cellulose (Ac-Di-Sol, manufactured by FMC International Co., Ltd.), polyvinyl pyrrolidone and low substituted hydroxypropyl cellulose or any combinations thereof) one or more excipients and any combinations thereof. The core can be produced by using routine techniques known in the art such as, but not limited to, direct blending, dry granulation (roller compaction), wet granulation (high shear granulation), milling or sieving, drying (if wet granulation is used), extrusion/spheronization, balling or compression, and, optionally, coating. Alternatively, the core can be formed by spraying the active agent on to an inactive (or inert) carrier or sphere using routine techniques known in the art. Binders can be used when spraying the active agent on to inactive carrier. Inactive carriers or spheres upon which active agents can be sprayed are well known in the art. Specifically, examples of such spheres that can be used, include, but are not limited to, a sphere of sucrose, a sucrose and starch sphere (such as NON-PARIEL-101, NON-PARIEL-105 produced by Freund Industrial Co., Ltd.) or a spherically granulated product of a crystalline cellulose sphere or a crystalline cellulose and lactose. An active agent layer is formed when the active agent is sprayed on to the inactive carrier or sphere.

The solid particle can also contain a protective or intermediate layer between the core and the enteric coating. The purpose of the protective layer is to prevent direct contact of the active agent (or active agent layer) with the enteric coating. The protective layer is formed on and around the core using routine techniques known in the art. For example, the components of the intermediate layer can diluted with purified water and the like and the mixture sprayed in liquid form to coat the core containing the active agent. At the time the protective layer is being applied, a binding agent (also known as a binder), such as hydroxypropylcellulose, can optionally be used (alternatively, the hydroxypropylcellulose can be included in the core as a binder).

The protective layer can be made from saccharides, such as sucrose (purified white sugar (those pulverized (powder sugar) and those not pulverized) and the like), starch saccharide such as, corn starch, lactose, honey and sugar alcohol (such as D-mannitol, erythritol and the like) appropriately compounded with polymeric base materials such as low substituted hydroxypropylcellulose, hydroxypropylcellulose, hydroxypropyl methylcellulose (for example, TC-5 and the like), polyvinyl pyrrolidone, polyvinyl alcohol, methylcellulose and hydroxyethyl methylcellulose as described in WO WO 2004/035020, the contents of which are herein incorporated by reference. One or more pharmaceutically acceptable excipients (such as, but not limited to, one or more film formers (such as Hypromellose 2910), one or more glidants (such as talc), one or more masking agents, one or more pigments (such as titanium dioxide), one or more anti-adherants (such as talc), one or more antistatic agents (such as, titanium oxide, talc and the like) or any combinations thereof can also be added to the protective layer if necessary. The protective layer is applied in the amount of about 0.02 part by weight to about 1.5 parts by weight based on 1 part by weight of the solid particles containing the active agent, and preferably about 0.05 part by weight to about 1 part by weight.

As mentioned above, the first granule also contains a first enteric coating. The first enteric coating surrounds the core and releases the active agent from the solid particle at a pH of about 5.0 to about 5.5. Preferably, the first enteric coating releases the active agent from the solid particle at a pH of about 5.5. This first enteric coating that releases the active agent from the solid particle at a pH of about 5.0 to about 5.5 in the proximal and distal segments of the small intestine.

The first enteric coating is coated on and surrounds the core (which may or may not contain a protective layer). Any enteric coating that will result in the release of the active agent at a pH of about 5.0 to about 5.5 can be used in the pharmaceutical composition. An example of a first enteric coating is a methacrylic acid copolymer dispersion, such as EUDRAGIT® L 30 D-55 (Evonik Industries, Germany) and EUDRAGIT® 100-55. Other examples of materials that can be used for the first enteric coating include, but are not limited to, hypromellose phthalate (HP-50 or HP-55), polyvinyl acetate phthalate, cellulose acetate phthalate, hypromellose acetate succinate.

As also mentioned above, the pharmaceutical composition contains at least a second solid particle. The components of the second solid particle are identical to the components described above for the first solid particle (namely, in terms of the core, protective layer, etc). The difference between the first solid particle and the second solid particle is the enteric coating, specifically, the second enteric coating. The second enteric coating surrounds the core and releases the active agent from the solid particle at a pH of about 6.2 to about 6.8. Preferably, the second enteric coating releases the active agent from the solid particle at a pH of about 6.75. The second enteric coating releases the active agent from the solid particle at a pH of about 6.2 to about 6.8 in the more distal segments of the small intestine.

The second enteric coating is coated on and surrounds the core (which may or may not contain a protective layer). Any enteric coating that will result in the release of the active agent at a pH of about 6.2 to about 6.8 can be used in the pharmaceutical composition. An example of a second enteric polymer is mixture of a methacrylic copolymer Type B and a methacrylic copolymer Type A. The methacrylic copolymer Type B and the methacrylic copolymer Type A are in a ratio of 4:1 to 1:4, preferably in a ratio of 3:1. An example of a methacrylic copolymer Type B is EUDRAGIT® S-100 and a methacrylic copolymer Type A is EUDRAGIT® L-100. Another material which can optionally be used as a second enteric coating is hypromellose acetate succinate or a mixture of different grades of hypromellose acetate succinate with varying degrees of substitution, such as those provided for in Table A, below.

TABLE A*

| Grade | pH solubility in McIvaine's Buffer Solution |
|---|---|
| LF** | ≧5.5 |
| MF** | ≧6.0 |
| HF** | ≧6.8 |
| LG | ≧5.5 |
| MG | ≧6.0 |
| AS/HG | ≧6.8 |

*The polymers listed in this Table A are available as Shin-Etsu AQOAT Enteric Coating Agents from Shin-Etsu Chemical Co., Ltd., Japan.
**F is fine power grade (average particle size is about 5 μm).

More specifically, HF grade could be used to obtain a pH of release starting at 6.8. Moreover, the HF or HG grades and MF or MG grades could be mixed in a ratio of 1:3 to obtain a pH of release of the active agent starting at a pH of about 6.2. Release of the active agent at a pH of about 6.5 could be obtained using a 5:3 ratio of HF to MF. Release of the active agent at a pH of about 6.75 could be obtained using a 15:1 ratio of HF to MF. Release of the active agent at a pH of 6.4 could be obtained using a ratio of 1.1 of HF to MF.

One or more pharmaceutically acceptable excipients (such as, but not limited to, one or more masking agents (such as titanium oxide and the like)), one or more anti-adherants (such as talc), one or more glidants (such as talc), one or more antistatic agents (such as, titanium oxide, talc and the like), one or more pigments (such as titanium dioxide), one or more plasticizers (such as polyethylene glycol, triethyl citrate, etc), or one or more surfactants (such as Polysorbate 80), or any combinations thereof can also be added to the first enteric coating, the second enteric coating or both the first enteric coating and the second enteric coating if necessary. Additional examples of plasticizers and surfactants that can be used are described in WO 2004/035020, the contents of which are herein incorporated by reference.

The amount of the first and second enteric coatings used in the first and second solid particles is about 10% by weight to about 70% by weight based on the total amount of each solid particle before the coating is applied, preferably about 10% by weight to about 50% by weight and more preferably about 15% by weight to about 30% by weight.

The first solid particles are present in the composition in the amount of from about 15% to about 50% by weight of the pharmaceutical composition, preferably about 25% by weight. The second solid particles are present in the pharmaceutical composition in an amount from about 50% to about 85% by weight of the pharmaceutical composition, preferably about 75% by weight. Thereupon, the preferred ratio of the first solid particles to the second solid particles contained in the pharmaceutical composition is 3:1.

As mentioned above, the inventors have found that the administration of the pharmaceutical compositions of the present invention with a high fat meal leads to an increase in the systemic exposure of the active agent after administration of such a high fat meal. While not wishing to be bound by any theory, it is believed that the discovery of this increase in systemic exposure is the result of the second solid particles and their specific interaction with food.

The methods of the present are particularly desirable for use in treating gastrointestinal disorders, particularly, but not limited to, symptomatic GERD, dyspepsia and heart burn. In addition, the methods of the present invention can be used to treat a patient suffering from chronic cough.

Many types of continuous drug release dosage forms are known in the art. For example, controlled or extended release, and pulsed release dosage forms are known. Any type of continuous drug release dosage form can be used in the present invention, including matrix systems, osmotic pumps, and membrane controlled systems (also referred to as reservoir systems). Each of these systems is described in greater detail below. A detailed discussion of such dosage forms may also be found in: (i) *Handbook of pharmaceutical controlled release technology*, ed. D. L. Wise, Marcel Dekker, Inc. New York, N.Y. (2000), and (ii) *Treatise on controlled drug delivery, fundamentals, optimization, and applications*, ed. A. Kydonieus, Marcel Dekker, Inc. New York, N.Y. (1992).

Matrix systems are well known in the art. In a matrix system, the drug is homogenously dispersed in a polymer and optionally, conventional excipients. This so-called admixture is typically compressed under pressure to produce a tablet. The drug is released from this tablet by diffusion and erosion. Matrix systems typically employ a pharmaceutically acceptable polymer such as a water-soluble hydrophilic polymer, or a water insoluble hydrophobic polymer (including waxes). One skilled in the art would readily be able to determine the type of pharmaceutically acceptable polymer to be used using routine techniques to those known in the art.

The pharmaceutical compositions of the present invention also typically include pharmaceutically acceptable excipients. As is well known to those skilled in the art, pharmaceutical excipients are routinely incorporated into solid dosage forms. This typically is done to ease the manufacturing process as well as to improve the performance of the pharmaceutical composition. Common excipients include, but are not limited to, diluents or bulking agents, lubricants, binders, etc.

Diluents, or fillers, can be added to, for example, increase the mass of an individual dose to a size suitable for tablet compression. Suitable diluents include, but are not limited to, powdered sugar, calcium phosphate, calcium sulfate, microcrystalline cellulose, lactose, mannitol, kaolin, sodium chloride, dry starch, xylitol and sorbitol.

Lubricants can be incorporated into a pharmaceutical composition for a variety of reasons. They reduce friction between the granulation and die wall during compression and ejection. This prevents, for example, a granulate from sticking to the tablet punches, and facilitates its ejection from the tablet punches. Examples of suitable lubricants include, but are not limited to, talc, stearic acid, vegetable oil, calcium stearate, zinc stearate, magnesium stearate, solid polyethylene glycols, sodium stearyl fumarate, silica gel, glyceryl behenate mixtures thereof and other substances with lubricating properties.

Glidant's can also be incorporated into a pharmaceutical composition, typically for purposes of improving the flow characteristics of the granulation. Examples of suitable glidant's include, but are not limited to, talc, silicon dioxide, and cornstarch.

Binders also may be incorporated into the pharmaceutical composition of the present invention. Binders are typically utilized if the manufacture of the dosage form employs a granulation step. Examples of suitable binders include povidone (such as polyvinylpyrrolidone), sugars (such as sucrose), xanthan gum, cellulose gums such as carboxymethylcellulose, methyl cellulose, hypromellose, microcrystalline cellulose, hydroxycellulose, hydroxypropylcellulose, mallodextrin gelatin, starch, pregelatinized starch, and other pharmaceutically acceptable substances with cohesive properties.

Other excipients that may be incorporated into the pharmaceutical composition include absorption accelerators, absorbents, effervescent agents, emulsifers, disintegrating agents, humectants, preservatives, solution retarders, solubility enhancing agents, buffers, surfactants, suspending agents, sweeteners, wetting agents or any other pharmaceutically acceptable excipient commonly used in the pharmaceutical industry.

Examples of "absorption accelerators" that can be used in the present invention include, but are not limited to, quaternary ammonium compounds. Examples of "absorbents" that can be used in the present invention include, but are not limited to, kaolin and bentonite. Examples of "effervescent agents" that can be used in the present invention are effervescent couples such as, but not limited to, an organic acid and a carbonate or bicarbonate. Suitable organic acids include, but are not limited to, citric, tartaric, malic, fumaric, adipic, succinic, and alginic acids and anhydrides and acid salts. Suitable carbonates and bicarbonates include, but are not limited to, sodium carbonate, sodium bicarbonate, potassium carbonate, potassium bicarbonate, magnesium carbonate, sodium glycine carbonate, L-lysine carbonate and arginine carbonate. Examples of "emulsifiers" that can be used in the present invention include, but are not limited to, ethyl alcohol, isopropyl alcohol, ethyl carbonate, ethyl acetate, benzyl alcohol, benzyl benzoate, propylene glycol, 1,3-butylene glycol, dimethylformamide, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like. Examples of "disintegrating agents" that can be used in the present invention include, but are not limited to, lightly cross-linked polyvinyl pyrrolidone, corn starch, potato starch, maize starch and modified starches, agar-agar, calcium carbonate, sodium carbonate, alginic acids, croscarmellose sodium, crospovidone, sodium starch glycolate and mixtures thereof. Examples of "humectants" that can be used in the present invention, include, but are not limited to, glycerol. Examples of "preservatives" that can be used in the present invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol or quaternary compounds such as benzalkonium chloride. Examples of "solution retarders" that can be used include in the present invention include, but are not limited to, paraffin. Examples of "solubility enhancing agents" that can be used in the present invention include, but are not limited to, co-solvents such as ethanol or propylene glycol, surfactants and polymeric substances such as polysorbates, polyalkylene glycols, poloxamers or polyvinylpyrrolidone, and oily fatty acids and their mono- or diglyceryl esters such as linoleic acid or glyceryl monolaurate. Examples of suitable "buffers" that can be used in the present invention include, but are not limited to, phosphate, acetate, citrate, succinate and histidine buffers. The term "surfactant" is used in its conventional sense in this invention. Any surfactant is suitable, whether it is amphoteric, non-ionic, cationic or anionic. Examples of suitable surfactants include, but are not limited to, sodium lauryl sulfate, monooleate monolaurate, monopalmitate, monstearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, polyoxyethylene sorbitan fatty acid esters (e.g., the commercially available Tween®s, such as, Tween® 20 and Tween® 80 (ICI Speciality Chemicals)), polyethylene glycols (e.g., Carbowaxs 3550® and 934® (Union Carbide)), poloxamers (e.g., Pluronics F68® and F108®, which are block copolymers of ethylene oxide and propylene oxide); polyoxyethylene castor oil derivatives or mixtures thereof. Examples of "suspending agents" that can be used include in the present invention include, but are not limited to, carboxymethylcelluose, veegum, tragacanth, bentonite, methylcellulose and polyethylene glycols. Examples of "sweeteners" that can be used in the present invention include, but are not limited to, any natural or artificial sweetener such as, but not limited to, sucrose, xylitol, sodium saccharin, cyclamate, aspartame and acsulfame. Examples of flavoring agents are Magnasweet®, bubble gum flavor, fruit flavors and the like. Examples of "wetting agents" that can be used in the present invention include, but are not limited to, ammonium lauryl sulfate and sodium lauryl sulfate.

The amount of excipients used in the pharmaceutical composition will correspond to that typically used in a matrix system. The total amount of excipients, fillers and the like typically will vary from about 10% to about 80% by weight of the pharmaceutical composition.

Matrix dosage forms of pharmaceutical compositions are generally prepared using standard techniques well known in the art. Typically, they are prepared by dry blending the polymer, filler, drug, and other excipients followed by granulating the mixture using an alcohol until proper granulation is obtained. The granulation is done by methods known in the art. The wet granules are dried in a fluid bed dryer, sifted and ground to appropriate size. Lubricating agents are mixed with the dried granulation to obtain the final pharmaceutical composition.

In an osmotic pump system, a tablet core is encased by a semipermeable membrane having at least one orifice. The semipermeable membrane is permeable to water, but impermeable to the drug. When the system is exposed to body fluids, water will penetrate through the semipermeable membrane into the tablet core containing osmotic excipients and the active drug. Osmotic pressure increases within the pharmaceutical composition and drug is released through the orifice in an attempt to equalize pressure.

In more complex pumps, the tablet core contains multiple internal compartments. For example, the first compartment may contain the drug and the second compartment may contain a polymer that swells on contact with fluid. After ingestion, this polymer swells into the drug containing compartment at a predetermined rate and forces drug from the pharmaceutical composition at that rate. Such pharmaceutical compositions are often used when a zero order release profile is desired.

Osmotic pumps are well known in the art and have been described in the literature. U.S. Pat. Nos. 4,088,864, 4,200,098, and 5,573,776, all of which are hereby incorporated by reference, describe osmotic pumps and methods for their manufacture. Osmotic pumps containing compounds, such as omeprazole, have been described in U.S. Pat. No. 5,178,867, the contents of which are hereby incorporated by reference.

As a general guideline, osmotic pumps are typically formed by compressing a tablet of an osmotically active drug (or an osmotically inactive drug in combination with an osmotically active agent or osmagent) and then coating the tablet with a semipermeable membrane that is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts the drug and/or salt to form a solution or suspension of the drug. The drug solution or suspension is then pumped out through the orifice as fresh fluid is imbibed through the semipermeable membrane.

As previously mentioned, osmotic pumps may contain multiple distinct compartments. The first compartment may contain the drug as described above, and the second compartment may contain an expandable driving member consisting of a layer of a swellable hydrophilic polymer, which operates to diminish the volume occupied by the drug, thereby delivering the drug from the device at a controlled rate over an extended period of time. Alternatively, the compartments may contain separate doses of the drug.

Typical materials for the semipermeable membrane include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586, 3,541,005, 3,541,006, and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

The osmotic agent present in the pump, which may be used when the drug itself is not sufficiently osmotically active, are osmotically effective compounds soluble in the fluid that enters the pump, and exhibits an osmotic pressure gradient across the semipermeable wall against the exterior fluid. Osmotically effective osmagents useful for the present purpose include magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, mixtures thereof, and the like. The osmagent is usually present in an excess amount, and it can be in any physical form, such as particle, powder, granule, and the like. The osmotic pressure in atmospheres of the osmagents suitable for the invention will be greater than zero and generally up to about 500 atm, or higher.

The expandable driving member typically is a swellable, hydrophilic polymer which interacts with water and aqueous biological fluids and swells or expands to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be cross-linked or may not be cross-linked. The swellable, hydrophilic polymers can be lightly cross-linked, such cross-links being formed by covalent ionic bonds or hydrogen bonds. The polymers can be of plant, animal or synthetic origin. Hydrophilic polymers that can be used in for the present invention include poly(hydroxy alkyl methacrylate) having a molecular weight from 30,000 to 5,000,000; kappa carrageenan, polyvinylpyrrolidone having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose; cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

The term "orifice" as used herein refers to means and methods suitable for releasing the drug from an osmotic system. The expression includes one or more apertures or orifices which have been bored through the semipermeable membrane by mechanical procedures. Alternatively, it may be formed by incorporating an erodible element, such as a gelatin plug, in the semipermeable membrane. In cases where the semipermeable membrane is sufficiently permeable to the passage of drug, the pores in the membrane may be sufficient to release the active ingredient in amounts sufficient to meet the plasma threshold. In such cases, the term "passageway" refers to the pores within the membrane wall even though no bore or other orifice has been drilled there through. A detailed description of osmotic passageways and the maximum and minimum dimensions for a passageway are disclosed in U.S. Pat. Nos. 3,845,770 and 3,916,899, the disclosures of which are incorporated herein by reference.

Osmotic pumps can be manufactured by standard techniques. For example, in one embodiment, the drug and other ingredients that may be housed in one area of the compartment adjacent to the passageway, are pressed into a solid possessing dimension that corresponds to the internal dimensions of the area of the compartment the drug will occupy, or the drug and other ingredients and a solvent are mixed into a solid or semisolid form by conventional methods such as ballmilling, calendaring, stirring or rollmilling, and then pressed into a preselected shape. Next, a layer of a hydrophilic polymer is placed in contact with the layer of drug in a like manner, and the two layers surrounded with a semipermeable wall. The layering of drug formulation and hydrophilic polymer can be fabricated by conventional two-layer press techniques. The wall can be applied by molding, spraying or dipping the pressed shapes into a wall forming material. Another and presently preferred technique that can be use for applying the wall is the air suspension procedure. This procedure consists of suspending and tumbling the pressed agent and dry hydrophilic polymer in a current of air and a wall forming composition until the wall is applied to the agent-hydrophilic polymer composite. The air suspension procedure is described in U.S. Pat. No. 2,799,241; *J. Am. Pharm. Assoc.*, 48:451-459 (1979). Other standard manufacturing procedures are described in *Modern Plastics Encyclopedia*, Vol. 46, pp. 62-70 (1969); and in *Pharmaceutical Sciences*, by Remington, Fourteenth Edition, pp. 1626-1678 (1970), published by Mack Publishing Company, Easton, Pa.

Reservoir systems also are well known in the art. This technology is also commonly referred to as microencapsulation, bead technology, or coated tablets. Particles of the drug are encapsulated with pharmaceutically acceptable polymer. This polymer, and its relative quantity, offers a predetermined resistance to drug diffusion from the reservoir to the gastrointestinal tract. Thus drug is gradually released from the beads into the gastrointestinal tract and provides the desired sustained release of the compound.

These dosage forms of pharmaceutical compositions are well known in the art. U.S. Pat. Nos. 5,286,497 and 5,737,320, both of which are hereby incorporated by reference, describe such dosage forms and their methods of production. U.S. Pat. Nos. 5,354,556, 4,952,402, and 4,940,588, all of which are hereby incorporated by reference, specifically discuss using such technology to produce sustained release pharmaceutical compositions. As further guidance, however, a pellet is formed with a core of a drug, optionally in association with conventional excipients. This core is then coated with one, or more, pharmaceutically acceptable polymers. Often, the coating polymer is an admixture of a major proportion of a pharmaceutically acceptable water insoluble polymer and a minor proportion of a pharmaceutically acceptable water soluble polymer.

The central core may be prepared by a number of techniques known in the art. Typically the drug is bound to an inert carrier with a conventional binding agent. The inert carrier is typically a starch or sugar sphere. Before the drug is bound to the inert carrier, it is typically blended with conventional excipients to expedite its handling and to improve the properties of the final dosage form of the pharmaceutical composition. These excipients are identical to those described above for the matrix systems. The quantity of these excipients can vary widely, but will be used in conventional amounts. The central core is then produced by utilizing a binder or binding agent to attach the powdered drug blend to the solid carrier. This can be accomplished by means known in the art for producing pharmaceutical beads. Suitable means include utilization of a conventional coating pan, an automatic coating machine, or a rotogranulator. The production of these central cores is described in more detail in *Pharmaceutical Pelletization Technology*, ed. I. GhebreSellassie, Marcel Dekker, Inc. New York, N.Y. (1989).

The second major component of a reservoir system is the polymeric coating. As noted above, the polymeric coating is responsible for giving the beads their release characteristics. The polymeric coating may be applied to the central core using methods and techniques known in the art. Examples of suitable coating devices include fluid bed coaters and pan coaters. The application techniques are described in more detail in: i) *Aqueous polymeric coatings for pharmaceutical pharmaceutical compositions*, ed. J. W. McGinity, Marcel Dekker, Inc. New York, N.Y. (1997); and ii) *Pharmaceutical compositions: Tablets* Vol. 3. ed. H. A. Lieberman, L. Lachman and J. B. Schwartz, Marcel Dekker, Inc. New York, N.Y. pp. 77-287, (1990).

Examples of suitable polymers include ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane or mixtures thereof.

Once the beads have been prepared, they may be filled into capsules as is known in the art. Alternately, they may be pressed into tablets using techniques conventional in the art.

Pulsed release systems, the other broad category of modified release dosage forms of pharmaceutical compositions, are also well known in the art. Pulsed release systems generally involve a first drug release and a second drug release separated by a predetermined period of time or site of release. Pulsed release systems also may include a combination of immediate release and extended release. Multiple formulation configurations are suitable for pulsed release dosage forms of pharmaceutical compositions.

For example, osmotic pumps also are suitable for purposes of pulsatile drug release and have been described in U.S. Pat. Nos. 5,017,381 and 5,011,692, both of which are herein incorporated by reference. Generally, the osmotic pump containing the drug is formed and then overcoated with a layer of a drug to provide for two releases of the drug, one from the coating layer and another from the osmotic pump.

Particle or granule systems have also been proposed for purposes of providing a pulsed release of drug. Systems for the pulsed release of a drug typically use distinct populations of drug containing particles to achieve a pulsed release. The populations employ different coating polymers, such as those mentioned above, to release the drug at different points in time or location. For example, polymers having different dissolution pHs are commonly used for this purpose. Hence, one population of granules can be coated with a polymer that begins dissolving at a pH of 6 and another population of granules can be coated with a polymer that begins dissolving at a pH of 6.5 to achieve a pulsed release. In this manner, the first population of granules would release the drug in the upper small intestine while the second population of the granules would release the drug further down stream and therefore at a later time.

The pharmaceutical compositions of the present invention can be administered orally in the form of tablets, pills, or granules may be loose filled into capsules. The tablets can be prepared by techniques known in the art and contain a therapeutically effective amounts of the active ingredient and such excipients as are necessary to form the tablet by such techniques.

One skilled in the art, taking into account above teachings will be readily able to formulate pharmaceutical compositions containing the at least two solid particles described herein.

As discussed briefly herein, the pharmaceutical compositions of the present invention can be used to treat a patient suffering from a gastrointestinal disorder and in need of treatment thereof. Such a patient can be treated by administering to said patient a the pharmaceutical composition of the present invention containing a therapeutically effective amount of the first and second solid particles. Moreover, the pharmaceutical compositions of the present invention can also be used to treat a patient suffering from chronic cough and in need of treatment thereof. Such a patient can be treated by administering to said patient a pharmaceutical composition of the present invention containing a therapeutically effective amount of the first and second solid particles.

By way of example and not of limitation, examples of the present invention will now be given.

Example 1

Dexlansoprazole Capsules

Dexlansoprazole capsules (TAK-390MR capsules) are designed to provide prolonged blood levels of TAK-390. This is accomplished by combining two types of enteric coated granules into one capsule. One type of granule releases drug in the proximal region of the small intestine when the pH reaches approximately 5.0-5.5. The second type of granule releases drug more distally in the intestine when the pH reaches approximately 6.2-6.8. The components of the two types of granules are the same except for the enteric coating layer.

pH 5.0-5.5 Releasing Granules (Granules-LL)

The granules that release at approximately pH 5.0-5.5 are coated with Methacrylic Acid Copolymer Dispersion.

pH 6.2-6.8 Releasing Granules (Granules-H)

The granules that release at approximately pH 6.2-6.8 are coated with a mixture of Methacrylic Acid Copolymer Type A (pH 6 release) and Type B (pH 7 release).

Table 1, below, describes the types of polymers and the proportion of each granule type used in TAK-390MR Capsules.

TABLE 1

| | Granule Type | |
|---|---|---|
| | LL | H |
| pH of release (approximate) | 5.0-5.5 | 6.2-6.8 |
| Polymer Type | Methacrylic acid copolymer dispersion | Mixture of Methacrylic Acid Copolymer Type A and Methacrylic Acid Copolymer Type B |
| Proportion of TAK-390 Dose | 15%-50% by weight | 50-85% by weight % |

Capsule and Description

The granules are filled into HPMC (hypromellose) capsules.

Excipients

All excipients except for the HPMC capsules are compendial. None of the ingredients in TAK-390MR capsules is of human or animal origin.

Composition

The composition of the 30 mg, 60 mg and 90 mg capsules are described in Tables 2 and 3 below. Table 2 provides a range of values for the composition of Granules-LL. Table 3 provides a range of values for the composition of Granules-H.

TABLE 2

| Component of Granules-LL | Quantity per Capsule (mg) | | |
|---|---|---|---|
| | 30 mg | 60 mg | 90 mg |
| CORE GRANULES | | | |
| TAK-390 | 6.5-8.5 | 14-16 | 21.5-23.5 |
| Sugar Sphere (500 μm to 710 μm) | 12.8-14.9 | 9-11 | 14-16 |
| Stabilizer | 4.5-6.5 | 3-5 | 4-6 |
| Diluent | 5.0-30.0 | 5.0-30.0 | 5.0-30.0 |
| Distintegrant | 3.14-5.15 | 2-4 | 3.5-5.5 |
| Binder | 0.06-0.26 | 0.02-0.22 | 0.08-0.28 |
| Solvent*³ | q.s. | q.s. | q.s. |
| PROTECTIVE LAYER | | | |
| Film Former | 1.0-5.0 | 1.0-5.0 | 1.0-5.0 |
| Anti-Adherent | 0.4-3.0 | 0.4-3.0 | 0.4-3.0 |
| Pigment | 0.5-3.5 | 0.5-3.5 | 0.5-3.5 |
| Solvent*³ | q.s. | q.s. | q.s. |
| ENTERIC LAYER-L | | | |
| Pigment | 0.5-2.0 | 0.5-2.0 | 0.5-2.5 |
| Anti-adherent | 1.9-4.0 | 0.9-3.0 | 1.9-5.0 |
| Methacrylic Acid Copolymer Dispersion*¹ | 6.0-12.0*² | 6.0-12.0*² | 6.0-12.0*² |
| Plasticizer | 0.5-2.5 | 0.5-2.5 | 0.5-2.5 |
| Surfactant | 0.1-1.0 | 0.1-1.0 | 0.1-1.0 |
| Solvent*³ | q.s. | q.s. | q.s. |
| LUBRICATION | | | |
| Antistatic agent | 0.01-0.1 | 0.01-0.1 | 0.01-0.1 |
| Glidant | 0.01-0.1 | 0.01-0.1 | 0.01-0.1 |

*¹Lacquer suspension (amount of dry lacquer in suspension is about 30%)
*²Amount as dry lacquer substance
*³Evaporated during manufacturing

TABLE 3

| Component-Granules-H | Quantity per capsule (mg) | | |
|---|---|---|---|
| | 30 mg | 60 mg | 90 mg |
| CORE GRANULES | | | |
| TAK-390 | 21.5-23.5 | 43-46 | 66.5-68.5 |
| Sugar Sphere (500 μm to 710 μm) | 14-16 | 29-31 | 44-46 |
| Stabilizer | 5-7 | 11-13 | 17-19 |
| Diluent | 10.0-50.0 | 10.0-50.0 | 10.0-50.0 |
| Disintegrant | 3.5-6.0 | 8-10 | 12.5-15.0 |
| Binder | 0.10-0.50 | 0.10-.75 | 0.1-1.0 |
| Solvent* | q.s. | q.s. | q.s. |
| PROTECTIVE LAYER | | | |
| Film Former | 2.0-15.0 | 2.0-15.0 | 2.0-15.0 |
| Anti-adherent | 1.0-6.0 | 1.0-6.0 | 1.0-6.0 |
| Pigment | 1.3-3.2 | 3.72-5.2 | 6.0-8.1 |
| Solvent* | q.s. | q.s. | q.s. |
| ENTERIC LAYER-H | | | |
| Anti-adherent | 9.63-12.0 | 20.26-22.3 | 30.89-33.0 |
| Methacrylic Acid Copolymer Type B | 4.0-16.0 | 8.0-33.0 | 14.0-50.0 |
| Methacrylic Acid Copolymer Type A | 4.0-16.0 | 8.0-33.0 | 14.0-50.0 |
| Plasticizer | 1.12-3.0 | 3.24-5.0 | 5.36-7.5 |
| Dehydrated Alcohol* | q.s. | q.s. | q.s. |
| Purified Water* | q.s. | q.s. | q.s. |
| LUBRICATION | | | |
| Glidant | 0.01-0.1 | 0.01-0.1 | 0.01-0.1 |
| Antistatic agent | 0.01-0.1 | 0.01-0.1 | 0.01-0.1 |

*Evaporated during manufacturing

Methods for making Granules-LL and H and filling into capsules are described below.

Methods for Making Dexlansoprazole Granules-LL and H.

Dexlansoprazole Granules-LL

1. Binder is dissolved in solvent by stirring to prepare binder solution.
2. Layering powder consisting of Dexlansoprazole, stabilizer, diluent and disintegrant is prepared by mixing.
3. Sugar Spheres are charged and tumbled in an open rotary granulator.
4. Sugar Spheres are layered with the layering powder while being sprayed with the binder solution.
5. The dried granules are sieved.
6. Pigment is dispersed in solvent using a Dispersing Machine.
7. Film former is dissolved in solvent by stirring.
8. Middle coating solution is prepared by mixing the suspension of pigment, anti-adherent and solvent with the solution of film former using stirrer.
9. The Dexlansoprazole Granules are coated with the middle coating solution in a Fluid Bed Coater.
10. Pigment is dispersed in solvent using a Dispersing Machine.
11. Plasticizer and surfactant are dissolved in solvent by stirring.
12. The enteric coating solution for Granules-LL is prepared by mixing the suspension of pigment, anti-adherent, methacrylic acid copolymer dispersion and solvent with the solution of plasticizer and surfactant using stirrer.
13. Dexlansoprazole Granules are coated with the enteric coating solution for Granules-L in a Fluid Bed Coater.
14. The coated granules are sieved.
15. Dexlansoprazole Granules-LL are mixed with antistatic agent and glidant in a diffusion mixer.

Dexlansoprazole Granules-H
1. Binder is dissolved in solvent by stirring to prepare binder solution.
2. Layering powder consisting of Dexlansoprazole, stabilizer, diluent and disintegrant, is prepared by mixing.
3. Sugar spheres are charged and tumbled in an open rotary granulator.
4. Sugar spheres are layered with the layering powder while being sprayed with the binder solution.
5. The granules are sieved.
6. Pigment is dispersed in solvent using a dispersing machine.
7. Film former is dissolved in solvent by stirring.
8. Middle coating solution is prepared by mixing the suspension of pigment, anti-adherent and solvent with the solution of the film former using stirrer.
9. The Dexlansoprazole Granules are coated with the middle coating solution in a fluid bed coater.
10. The sieved granules are dried in a vacuum dryer.
11. Methacrylic Acid Copolymer Type B, Methacrylic Acid Copolymer Type A and plasticizer are dissolved in a mixture of dehydrated alcohol and purified water by stirring.
12. The enteric coating solution for Granules-H is prepared by mixing anti-adherent and the solution of Methacrylic Acid Copolymer Type B, Methacrylic Acid Copolymer Type A, plasticizer, dehydrated alcohol and purified water using stirrer.
13. The granules are coated with the enteric coating solution for Granules-H in a fluid bed coater.
14. The coated granules are sieved.
15. Dexlansoprazole Granules-H are mixed with antistatic agent and glidant in a diffusion mixer.

Dexlansoprazole Capsules
  Dexlansoprazole Granules-LL and Dexlansoprazole Granules-H are filled into capsules using an encapsulator.

Example 2

The Effect and Timing of Food on the Pharmacokinetics and Pharmacodynamics of TAK-390MR: Evidence for Dosing Flexibility Introduction
Proton pump inhibitors (PPIs) bind only to actively secreting proton pumps; therefore, dosing guidelines generally recommend that PPIs be administered 30 to 60 minutes prior to a meal, such that drug is available when maximal stimulation of parietal cell activity occurs. However, dosing of esomeprazole within 15 minutes of a high-fat breakfast has been shown to have a negative effect on its absorption and bioavailability (both $C_{max}$ and AUC) (See, Sostek M B, et al. *Br J Clin Pharmacol.* 64:386-390 (2007)). Fifty-four percent (54%) of patients with poorly controlled GERD dose their PPIs suboptimally in relation to meals. Therefore, a PPI that can be administered without regard to food intake would offer dosing flexibility and could have a positive effect on compliance.

Purpose of Study
The purpose of this study was to evaluate the effect of food on the pharmacokinetics (PK) and pharmacodynamics (PD) of TAK-390 after a single oral dose of TAK-390 MR 90 mg, made as described in Example 1.

Methods
Study Design
This study was a phase 1, open-label, randomized, single-dose, 4-way crossover study conducted at a single center. Healthy adult subjects were randomized on Day 1 of Period 1 to 1 of 4 sequence groups that determined the order in which patients received the 4 different dosing regimens (See, Table 4, below). During each of the 4 crossover periods, subjects received a single dose of placebo on Day 1 and a single dose of TAK-390MR 90 mg on Day 3 at about 8:00 AM after an overnight fast. There was a minimum washout interval of at least 5 days between the last dose in a period and the first dose in the subsequent period.

Inclusion Criteria
Healthy male and female subjects aged 18-55 years with negative *H. pylori* test results at screening were eligible to participate in this study.

Pharmacokinetic Evaluations and Statistical Analyses
The PK profile of TAK-390MR was assessed through blood sampling before dosing and over a 24-hour period after dosing on Day 3 of each period. PK parameters for TAK-390 were estimated using standard noncompartmental methods and include: $t_{lag}$=time delay between drug administration and first observed concentration above the lower limit of quantitation; $t_{max}$=time to reach the observed maximum plasma concentration; $C_{max}$=observed maximum plasma concentration; and AUC=area under the plasma concentration vs time curve from time zero the last quantifiable concentration ($AUC_t$) and from time zero to infinity ($AUC_\infty$).

Statistical assessments of the food effect (fed regimens B, C, or D) relative to the fasting regimen (A) were made via point estimates and 90% CIs for the ratios for $C_{max}$, $AUC_t$, and $AUC_\infty$ for TAK-390. It was concluded that food had no effect if the 90% CIs for the ratios from the 2 regimens were within the bioequivalency range of 0.80 and 1.25.

Pharmacodynamic Evaluations and Statistical Analyses
Pharmacologic response was measured for each regimen on Days 1 and 3 of each period with 24-hour continuous intragastric pH monitoring using a Medtronic Digitrapper™ pH recorder (Medtronic, Inc., Minneapolis, Minn.).

Two PD parameters, mean intragastric pH and % time pH>4 over 24 hours post dose, were calculated using the medians of pH measurements during 15-minute intervals. The values for Day 1 were treated as baseline of each regimen.

For each regimen, PD parameters at baseline (Day 1) and Day 3, as well as changes from baseline, were summarized using descriptive statistics.

ANOVA models on changes in PD parameters from baseline to Day 3 were used to assess the effect of the changes in the PK of TAK-390 on PD under different fasting/fed conditions. The statistical significance level for the tests was 0.05.

Safety Evaluation
Safety was monitored through adverse event (AE) reports, concomitant medication use, 12-lead electrocardiograms, physical examinations, vital sign assessments, and laboratory evaluations.

Results
Demographics
Forty-six of forty-eight subjects who were randomized to the 4 sequence groups and completed at least 2 dosing regimens were included in the PK and PD analyses. All 48 subjects were included in the safety analyses. They were primarily men (60%) and ranged in age from 19-53 years (mean±SD=32±11 years). Seventy-seven percent (77%) were white and twenty-three percent (23%) were black. Their mean±SD height was 172±10 cm, and their mean±SD weight was 76±12 kg.

Pharmacokinetics
When TAK-390MR was administered in the fed state (Regimen B), the $t_{lag}$ for TAK-390 was delayed by a mean of ~1 hour, and the $t_{max}$ was delayed by a mean of ~2 hours compared with administration of TAK-390MR in the fasting state (Regimen A) (See, Table 5, below). When TAK-390MR was administered 5 minutes (Regimen C) or 30 minutes (Regimen D) before a high-fat breakfast, mean TAK-390 $t_{lag}$ and $t_{max}$ values were similar to those obtained when TAK-390MR was administered in the fasting state (Regimen A). Mean TAK-390 $C_{max}$ and $AUC_t$ values increased 17-31% when TAK-390MR was administered in the fed state (Regimen B) or 5 minutes before a meal (Regimen C), but was bioequivalent when administered 30 minutes before a meal (Regimen D) compared with administration in the fasted state (Regimen A) (See, Table 6, below). The mean plasma TAK-390 concentration vs time profiles for each regimen are shown in FIG. 1.

Pharmacodynamics

Figure 2:
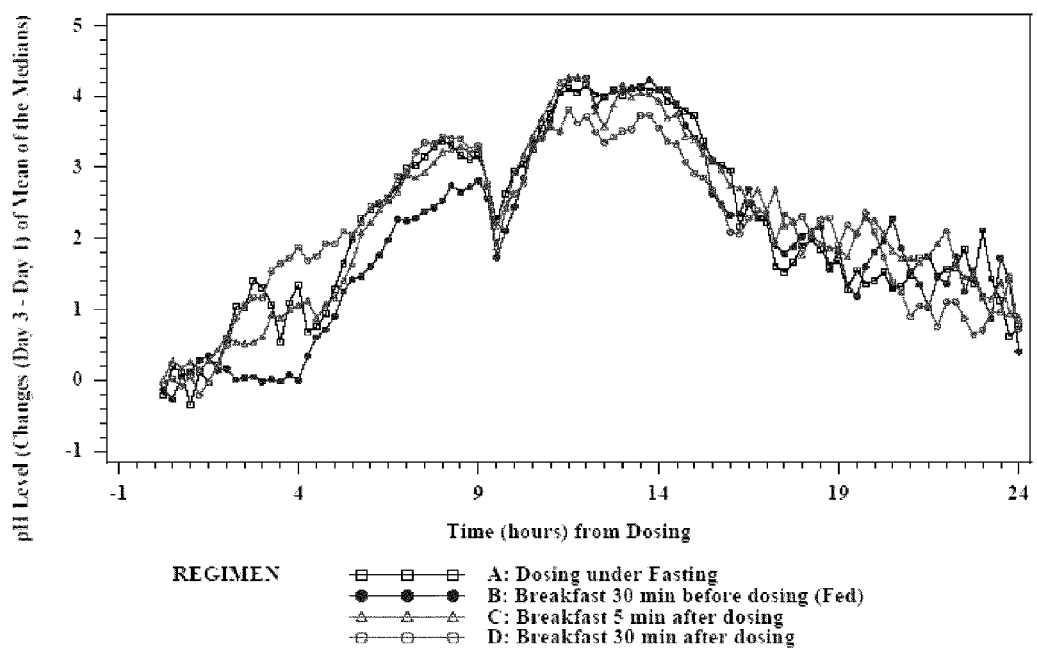
FIG. 2 illustrates that the intragastric pH results described in Example 2 suggest that the changes in TAK-390 pharmacokinetics under different fasting/fed conditions did not have a relevant effect on the pharmacodynamics of TAK-390MR.

Overall, the intragastric pH results suggest that the changes in TAK-390 PK under different fasting/fed conditions did not have a relevant effect on the PD of TAK-390MR (See, Table 7 and FIG. 2). There were no statistically significant differences among any of the pairwise comparisons of the fed regimens with the fasting regimen for the change from baseline (Day 3 minus Day 1) over the 24-hour postdose interval for mean intragastric pH. The only statistically significant difference that occurred in the pairwise comparisons was between fed (Regimen B) and fasted (Regimen A) for the percentage of time with intragastric pH>4; the difference between the 2 regimens was 8%.

Safety

No consistent, clinically important changes were observed in any of the study safety parameters when TAK-390MR was administered under fasting or various fed conditions. Nineteen subjects (40%) experienced at least 1 treatment-emergent adverse event (AE); there was little difference among the regimens in the number of subjects experiencing at least 1 AE. No deaths or serious AEs occurred, but 1 subject prematurely discontinued due to an AE (hepatic enzyme increase) during the washout interval following Period 1 in Regimen C.

CONCLUSIONS

There was a significant but modest increase in TAK-390 exposure following administration of TAK-390MR under various fed conditions compared with the fasting state (12-31% increase in $C_{max}$; 9-12% increase in the AUCs). The changes in TAK-390 PK following dosing under different fasting/fed conditions did not produce relevant differences in intragastric pH. The pH results indicate that TAK-390MR can be administered without regard to food or the timing of food. A PPI that can be administered without regard to food intake offers improved dosing flexibility and can have a positive effect on compliance.

TABLE 4

Treatment Sequences and Dosing Regimens

| Regimen | Timing of Dose of TAK-390MR 90 mg or Placebo |
|---|---|
| A | Dosed under fasting conditions |
| B | Fed State: Dosed 30 min after the start of a high-fat breakfast |
| C | Dosed 5 min before a high-fat breakfast |
| D | Dosed 30 min before a high-fat breakfast |

TABLE 5

Summary of the Effect of Food and Timing of Food on PK Parameter Estimates Following a Single Oral Dose of TAK-390MR

| Regimen | Measure | $t_{lag}$ h | $t_{max}$ h | $C_{max}$ ng/mL | $AUC_t$ ng·h/mL | $AUC_\infty$ ng·h/mL |
|---|---|---|---|---|---|---|
| A | N | 46 | 46 | 46 | 46 | 37 |
|   | Mean | 0.87 | 5.38 | 1486 | 6996 | 7058 |
|   | CV % | 70 | 36 | 54 | 53 | 53 |
| B | n | 46 | 46 | 46 | 46 | 37 |
|   | Mean | 1.91 | 7.63 | 1825 | 7999 | 8157 |
|   | CV % | 45 | 24 | 36 | 48 | 49 |
| C | n | 46 | 46 | 46 | 46 | 37 |
|   | Mean | 0.49 | 5.94 | 1653 | 7975 | 8198 |
|   | CV % | 136 | 41 | 43 | 47 | 48 |
| D | n | 46 | 46 | 46 | 46 | 37 |
|   | Mean | 0.53 | 4.73 | 1597 | 7448 | 7970 |
|   | CV % | 92 | 60 | 48 | 52 | 50 |

TABLE 6

Bioavailability of TAK-390 Following a Single Oral Dose of TAK-390MR Administered Under Various Fed Conditions Relative to Administration Under Fasting Conditions

| PK Parameter | Point Estimate | 90% CI |
|---|---|---|
| Regimen B vs Regimen A (Reference) | | |
| $C_{max}$ | 1.3065 | 1.1735-1.4547 |
| $AUC_t$ | 1.1901 | 1.1249-1.2591 |
| $AUC_\infty$ | 1.2050 | 1.1449-1.2683 |
| Regimen C vs Regimen A (Reference) | | |
| $C_{max}$ | 1.1684 | 1.0494-1.3009 |
| $AUC_t$ | 1.1910 | 1.1257-1.2600 |
| $AUC_\infty$ | 1.2096 | 1.1484-1.2740 |
| Regimen D vs Regimen A (Reference) | | |
| $C_{max}$ | 1.1165 | 1.0026-1.2432 |
| $AUC_t$ | 1.0903 | 1.0305-1.1535 |
| $AUC_\infty$ | 1.1483 | 1.0887-1.2112 |

TABLE 7

Analysis of Mean Intragastric pH and Percentage of Time With Intragastric pH >4 During the Total 24-hour Postdose Time Interval on Day 1 (Placebo) and on Day 3 (TAK-390MR) and of the Change From Baseline (Day 3 Minus Day 1)

| Regimen | Result for Each Dosing Regimen | | | | P Value[a] for Pairwise Comparison | | |
|---|---|---|---|---|---|---|---|
|  | A | B | C | D | B vs A[b] | C vs A[b] | D vs A[b] |
| Mean Intragastric pH | | | | | | | |
| Day 1 (Placebo) | 2.28 | 2.27 | 2.19 | 2.41 | 0.97 | 0.57 | 0.38 |
| Day 3 (TAK-390MR) | 4.46 | 4.25 | 4.43 | 4.53 | 0.09 | 0.71 | 0.60 |
| Δ from Baseline (Day 3 Minus Day 1)$ | 2.18 | 1.97 | 2.24 | 2.13 | 0.25 | 0.81 | 0.70 |
| % Time Intragastric pH >4 | | | | | | | |
| Day 1 (Placebo) | 17 | 18 | 16 | 19 | 0.90 | 0.55 | 0.55 |
| Day 3 (TAK-390MR) | 64 | 57 | 62 | 66 | <0.01** | 0.22 | 0.54 |

TABLE 7-continued

Analysis of Mean Intragastric pH and Percentage of Time With Intragastric pH >4 During the Total 24-hour Postdose Time Interval on Day 1 (Placebo) and on Day 3 (TAK-390MR) and of the Change From Baseline (Day 3 Minus Day 1)

| Regimen | Result for Each Dosing Regimen | | | | P Value[a] for Pairwise Comparison | | |
|---|---|---|---|---|---|---|---|
| | A | B | C | D | B vs A[b] | C vs A[b] | D vs A[b] |
| Δ from Baseline (Day 3 Minus Day 1)$ | 47 | 39 | 46 | 47 | 0.02* | 0.64 | 0.99 |

$Adjusting for the effect of the breakfast timing relative to dosing on pH
[a]P values are from an ANOVA with effects for regimen, sequence, period, and subject nested within sequence.
[b]Regimen A was defined as the reference regimen.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A method of treating heartburn, acid reflux or gastroesophageal reflux disease in a patient in need of treatment thereof, the method comprising the steps of:
   a) obtaining a pharmaceutical composition comprising dexlansoprazole from a group of pharmaceutical compositions comprising proton pump inhibitors; and
   b) administering to a patient suffering from heartburn, acid reflux or gastroesophageal reflux, regardless of whether the patient is under fasted or fed conditions, a therapeutically effective amount of the pharmaceutical composition obtained in step a), wherein the pharmaceutical composition comprises: (i) a first solid particle, wherein said first solid particle comprises dexlansoprazole and a first enteric coating, wherein the first enteric coating releases the proton pump inhibitor from the solid particle at a pH of about 5.0 to about 5.5; and (ii) a second solid particle, wherein said second solid particle comprises dexlansoprazole and a second enteric coating, wherein the second enteric coating releases the proton pump inhibitor from the solid particle at a pH of about 6.2 to about 6.8; wherein the first solid particle comprises from about 15% to about 50% by weight of the pharmaceutical composition and the second solid particle comprises from about 50% to about 85% by weight of the pharmaceutical composition.

2. The method of claim 1, wherein the first enteric coating has a pH of about 5.5.

3. The method of claim 1, wherein the second enteric coating has a pH of about 6.75.

4. The method of claim 1, wherein the changes in pharmacokinetics after administration to the patient of a single dose of a therapeutically effective amount of the pharmaceutical composition comprising dexlansoprazole under fasting or fed conditions does not produce statistically significant changes in intragastric pH.

5. The method of claim 1, wherein the patient is suffering from heart burn.

6. The method of claim 1, wherein the patient is suffering from acid reflux.

7. The method of claim 1, wherein the patient is suffering from gastroesophageal reflux.

8. The method of claim 1, wherein the pharmaceutical composition comprising dexlansoprazole is in the form of a tablet or a capsule.

9. The method of claim 1, wherein the administration of the composition to a human subject in a fed state is bioequivalent to administration of the composition to a human subject in a fasted state.

10. The method of claim 9, wherein bioequivalency of the composition is established by a 90% Confidence Interval for AUC which is between 0.80 and 1.25.

11. The method of claim 9, wherein bioequivalency of the composition is established by a 90% Confidence Interval for $C_{max}$, which is between 0.80 and 1.25.

12. The method of claim 1, wherein the pharmaceutical composition comprising dexlansoprazole administration provides a mean intragastric pH of between about 4.2 and about 4.5 on day 3 following administration regardless of whether the dexlansoprazole was administered in a fed or fasted state.

* * * * *